United States Patent
Koyata et al.

(10) Patent No.: US 8,557,599 B2
(45) Date of Patent: Oct. 15, 2013

(54) METHOD FOR AUTOMATIC DETERMINATION OF SAMPLE

(75) Inventors: Atsushi Koyata, Tokyo (JP); Hiroyuki Yokoi, Tokyo (JP)

(73) Assignee: Mitsubishi Chemical Medience Corporation, Tokyo (JP)

( * ) Notice: Subject to any disclaimer, the term of this patent is extended or adjusted under 35 U.S.C. 154(b) by 0 days.

(21) Appl. No.: 13/323,561

(22) Filed: Dec. 12, 2011

(65) Prior Publication Data

US 2012/0142043 A1 Jun. 7, 2012

Related U.S. Application Data

(63) Continuation of application No. 11/572,749, filed as application No. PCT/JP2005/013767 on Jul. 27, 2005, now abandoned.

(30) Foreign Application Priority Data

Jul. 27, 2004 (JP) ................................. 2004-218142

(51) Int. Cl.
*G01N 21/00* (2006.01)
*G01N 21/75* (2006.01)
*G01N 33/48* (2006.01)

(52) U.S. Cl.
USPC ........................... 436/164; 422/82.09; 356/39

(58) Field of Classification Search
USPC .......................................................... 436/164
See application file for complete search history.

(56) References Cited

U.S. PATENT DOCUMENTS

| | | | |
|---|---|---|---|
| 3,861,877 A | 1/1975 | Matharani et al. | |
| 4,252,536 A | 2/1981 | Kishimoto et al. | |
| 4,303,336 A | 12/1981 | Cullis | |
| 4,668,617 A | 5/1987 | Furuta et al. | |
| 5,114,860 A | 5/1992 | Hayashi | |
| 6,083,754 A * | 7/2000 | Sakurai et al. | 436/52 |
| 2005/0101025 A1 | 5/2005 | Ho | |

FOREIGN PATENT DOCUMENTS

| | | |
|---|---|---|
| EP | 1054250 A1 | 11/2000 |
| JP | 05-026876 A | 2/1993 |
| JP | 06-265554 A | 9/1994 |
| JP | 10-019903 A | 1/1998 |
| JP | 10-048214 A | 2/1998 |
| JP | 10-274656 A | 10/1998 |

OTHER PUBLICATIONS

International Search Report issued in PCT/JP2005/013767, mailed Aug. 23, 2005.
Extended Supplementary European Search Report, issued in European Patent Application No. 05767461, mailed Jan. 31, 2012.

* cited by examiner

*Primary Examiner* — Sam P Siefke
*Assistant Examiner* — Bryan Kilpatrick
(74) *Attorney, Agent, or Firm* — Heslin Rothenberg Farley & Mesiti P.C.; Andrew K. Gonsalves, Esq.

(57) ABSTRACT

A method of determining a kind of a sample, in a method for analyzing a substance by the steps of supplying the sample to be analyzed to a reaction system by a supplying means comprising a transparent region composed of a transparent material, reacting a reagent for detecting the substance with the sample in the reaction system, and analyzing a signal derived from a product obtained by the reaction, characterized by irradiating the transparent region with light in the supplying step, and analyzing an optical intensity of the light.

2 Claims, 3 Drawing Sheets

(A)        (B)

METHOD FOR AUTOMATIC DETERMINATION OF SAMPLE

CROSS-REFERENCE TO RELATED APPLICATIONS

This application is a continuation of U.S. patent application Ser. No. 11/572,749, filed Jan. 26, 2007, now abandoned and published as US-2008/0096285-A1 on Apr. 24, 2008, which is a U.S. national phase application under 35 U.S.C. §371 of International Application No. PCT/JP2005/013767, filed Jul. 27, 2005, and published in Japanese as WO 2006/011531 on Feb. 2, 2006, which claims priority to Japanese Application No. 2004-218142, filed on Jul. 27, 2004, each of which is incorporated by reference herein in its entirety.

TECHNICAL FIELD

The present invention relates to a method for an automatic determination of a sample type, in a method for analyzing the sample, i.e., a method for analyzing a specific component contained in the sample such as body fluids, particularly blood.

BACKGROUND ART

It is clinically important to measure a specific component in blood, for example, antigens, antibodies, proteins, or endocrines. A serum or plasma is commonly used as a blood sample and, in this case, a serum or plasma is generally separated from whole blood as rapidly as possible to avoid hemolysis. This is because, when blood cells are contained in a sample or hemolysis occurs, for example, in an immunoassay, there is a possibility of the occurrence of the effects of hemolysis on an optical system, an inhibition of an immunoreaction by internal components of blood cells, an aggregation of insoluble carriers used as a solid phase caused by a membrane component of blood cells, or an interference by adsorption or the like. Therefore, it is a conventional procedure in general clinical laboratory tests to remove blood cells from collected whole blood by centrifugation and to use the resulting serum or plasma as a sample to be tested.

However, since a dedicated device such as a centrifuge is necessary for the removal of blood cells, and the procedure needs time and effort, it is preferable to use whole blood as a sample without pretreatment, for a general practitioner not having such a device or in an unrespited emergency test, and various methods have been proposed.

For example, Japanese Unexamined Patent Publication (Kokai) No. 10-48214 (patent reference 1) discloses a method for using completely hemolyzed whole blood by sonicating whole blood or mixing whole blood with a hypotonic solution. Japanese Unexamined Patent Publication (Kokai) No. 6-265554 (patent reference 2) discloses a method of analyzing a biochemical component of blood, comprising the steps of determining whether or not a sample contains blood cells; when the result that the sample contains blood cells is obtained, determining whether or not only one or more measurable items which can be analyzed by using a sample containing blood cells are selected; and when the result that only measurable item(s) which can be analyzed by using a sample containing blood cells are selected is obtained, stirring the sample and measuring the stirred sample.

However, the method for completely hemolyzing whole blood disclosed in the above patent reference 1 has several problems, for example, various states of hemolysis. Further, interferences which flow from the inside of blood cells to a reaction system, such as hemoglobin or substances derived from the cell nucleus, sometimes seriously affect the measurement by causing a nonspecific reaction or, particularly in an immunological assay, an interfering of immunoreaction.

With respect to the method of analyzing a biochemical component of blood disclosed in the above patent reference 2, a method of determining the kind of the sample (i.e., whether or not the sample contains blood cells) is not fully disclosed. The patent reference 2 only discloses that a means for determining the kind of a sample, such as a transmission optical sensor, may be located over cuvettes encapsulating a reagent, a sample, a diluent, or the like. Further, a concrete procedure and criterion for the determination are not disclosed in the patent reference 2, except for the disclosure that, when a sample contains blood cells, a hematocrit compensation should be carried out by stirring the sample.

[patent reference 1] Japanese Unexamined Patent Publication (Kokai) No. 10-48214

[patent reference 2] Japanese Unexamined Patent Publication (Kokai) No. 6-265554

SUMMARY OF THE INVENTION

Problems to be Solved by the Invention

An object of the present invention is to provide a method capable of automatically determining the kind of a sample, in a general-purpose automatic analyzer for not only a serum or plasma but also whole blood, without a step in which a measurer inputs or sets the type of the sample into the analyzer before the measurement. Another object is to provide a method capable of detecting a failure to apply a sample into the analyzer, simultaneously with the determination of the type of the sample. Still another object is to provide a method capable of simultaneously detecting a failure to mount a dispensing tip, in an automatic analyzer in which dispensing tips are mounted.

Means for Solving the Problems

These objects may be solved by the present invention, i.e., a method of determining a kind of a sample (preferably the presence or absence of a sample in a supplying means and/or a kind of a sample), in a method for analyzing a substance by the steps of supplying the sample suspected of containing the substance to be analyzed to a reaction system by a supplying means comprising a transparent region composed of a transparent material, reacting a reagent for detecting the substance with the sample in the reaction system, and analyzing a signal derived from a product obtained by the reaction, characterized by irradiating the transparent region with light in the supplying step, and analyzing an optical intensity of the light.

According to a preferred embodiment of the method of the present invention, the supplying means is a dispensing means in which a tip can be mounted (preferably, removably mounted) and liquid can be aspirated and poured out by means of the tip. That is, the present invention relates to a method of determining a kind of a sample (preferably the presence or absence of a sample in a tip and/or a kind of a sample, more preferably the mounting or detaching of a tip, the presence or absence of a sample in a tip, and/or a kind of a sample), in a method for analyzing a substance by the steps of supplying (preferably dispensing) the sample suspected of containing the substance to be analyzed to a reaction system by a dispensing means in which a tip is mounted and liquid can be aspirated and poured out by means of the tip, reacting a reagent for detecting the substance with the sample in the reaction system, and analyzing a signal derived from a product obtained by the reaction, characterized by irradiating a sample-holding portion of the tip with light in the supplying step (i.e., when the sample is aspirated into the tip), and analyzing an optical intensity of the light.

According to another preferred embodiment of the method of the present invention, the supplying means is a tube or a channel. That is, the present invention relates to a method of determining a kind of a sample (preferably the presence or absence of a sample in a supplying means and/or a kind of a sample), in a method for analyzing a substance by the steps of supplying the sample suspected of containing the substance to be analyzed to a reaction system by a tube or a channel comprising a transparent region composed of a transparent material, reacting a reagent for detecting the substance with the sample in the reaction system, and analyzing a signal derived from a product obtained by the reaction, characterized by irradiating the transparent region with light in the supplying step (i.e., when the sample passes through the tube or the channel), and analyzing an optical intensity of the light.

According to still another preferred embodiment of the method of the present invention, the sample is whole blood, a serum, or plasma.

The present invention relates to an apparatus for analyzing a substance by the steps of supplying a sample suspected of containing the substance to be analyzed to a reaction system by a supplying means, reacting a reagent for detecting the substance with the sample in the reaction system, and analyzing a signal derived from a product obtained by the reaction, characterized by comprising (a) a supplying means comprising a transparent region composed of a transparent material;
(b) an irradiating means capable of irradiating the transparent region with light in the supplying step;
(c) an optically analyzing means capable of analyzing a change in an optical intensity of the light; and
(d) a means for determining a kind of the sample by the optical intensity.

The determining means may comprise, for example, a means for storing a threshold value obtained from a previously measured value, a means for comparing a secondary measured value with the stored threshold value, a means for indicating a subsequent procedure (or a warning) according to the comparison result, and a means for outputting the comparison result (a warning means).

According to a preferred embodiment of the apparatus of the present invention, the supplying means is a dispensing means in which a tip can be mounted (preferably, removably mounted) and liquid can be aspirated and poured out by means of the tip. That is, the present invention relates to an apparatus for analyzing a substance by the steps of supplying (preferably dispensing) a sample suspected of containing the substance to be analyzed to a reaction system by a dispensing means in which a tip is mounted and liquid can be aspirated and poured out by means of the tip, reacting a reagent for detecting the substance with the sample in the reaction system, and analyzing a signal derived from a product obtained by the reaction, characterized by comprising (a) a dispensing means in which a tip can be mounted and liquid can be aspirated and poured out by means of the tip;
(b) an irradiating means capable of irradiating a sample-holding portion of the tip with light in the supplying step (i.e., when the sample is aspirated into the tip);
(c) an optically analyzing means capable of analyzing a change in an optical intensity of the light; and
(d) a means for determining a kind of the sample (preferably the presence or absence of a sample in a tip and/or a kind of a sample, more preferably the mounting or detaching of a tip, the presence or absence of a sample in a tip, and/or a kind of a sample) by the optical intensity.

According to a preferred embodiment of the apparatus of the present invention, the supplying means is a tube or a channel. That is, the present invention relates to an apparatus for analyzing a substance by the steps of supplying a sample suspected of containing the substance to be analyzed to a reaction system by a tube or a channel comprising a transparent region composed of a transparent material, reacting a reagent for detecting the substance with the sample in the reaction system, and analyzing a signal derived from a product obtained by the reaction, characterized by comprising (a) a tube or a channel comprising a transparent region composed of a transparent material;
(b) an irradiating means capable of irradiating the transparent region with light in the supplying step;
(c) an optically analyzing means capable of analyzing a change in an optical intensity of the light; and
(d) a means for determining a kind of the sample (preferably the presence or absence of a sample in the tube or the channel and/or a kind of the sample) by the optical intensity.

According to still another preferred embodiment of the apparatus of the present invention, the sample is whole blood, a serum, or plasma.

Effects of the Invention

According to the present invention, the kind of a sample can be automatically determined, and a step in which a measurer inputs or sets the kind of the sample into an analyzer before the measurement can be skipped. Therefore, the present invention is useful, particularly, for a general operator not having a dedicated device such as a centrifuge or for an unrespited emergency test. Further, according to the present invention, a failure to apply a sample into the analyzer can be detected, as well as the determination of the type of the sample. Furthermore, according to the present invention, a failure to mount a dispensing tip can be simultaneously detected in an automatic analyzer in which dispensing tips are mounted.

EXPLANATIONS OF REFERENCE SIGNS IN DRAWINGS

1 . . . automatic analyzer; 2 . . . measuring table; 3 . . . cartridge; 4 . . . tip; 5 . . . nozzle; 11 . . . light emitting diode;

12 . . . photodiode; 13 . . . operational amplifier for current-voltage conversion; 14AD . . . converter.

DETAILED DESCRIPTION OF THE INVENTION

The determining method of the present invention can be applied to a method for an automatic analysis of a sample, such as body fluids, particularly blood, so long as the automatic analyzing method comprises a step of supplying the sample to a reaction system. As the automatic analyzing method, there may be mentioned, for example, an automatic analyzing method comprising a step of supplying (for example, dispensing) a sample to a reaction system by a dispensing means in which a tip can be mounted and liquid can be aspirated and poured out by means of the tip, or an automatic analyzing method comprising a step of supplying a sample to a reaction system by a transfer means (for example, a tube or a channel) capable of aspirating the sample from one end thereof and transferring the sample from the other end thereof. Further, the analyzing apparatus of the present invention can be applied to an automatic analyzer equipped with a means for supplying a sample to a reaction system. As the automatic analyzer, there may be mentioned, for example, an analyzer equipped with a dispensing means in which a tip can be mounted and liquid can be aspirated and poured out by means of the tip, or an analyzer equipped with a transfer means (for example, a tube or a channel) capable of aspirating the sample from one end thereof and transferring the sample from the other end thereof.

An embodiment of an automatic analyzing method and an automatic analyzer to which the determining method of the present invention can be applied will be explained with reference to FIGS. 1 and 2.

Figure 1:
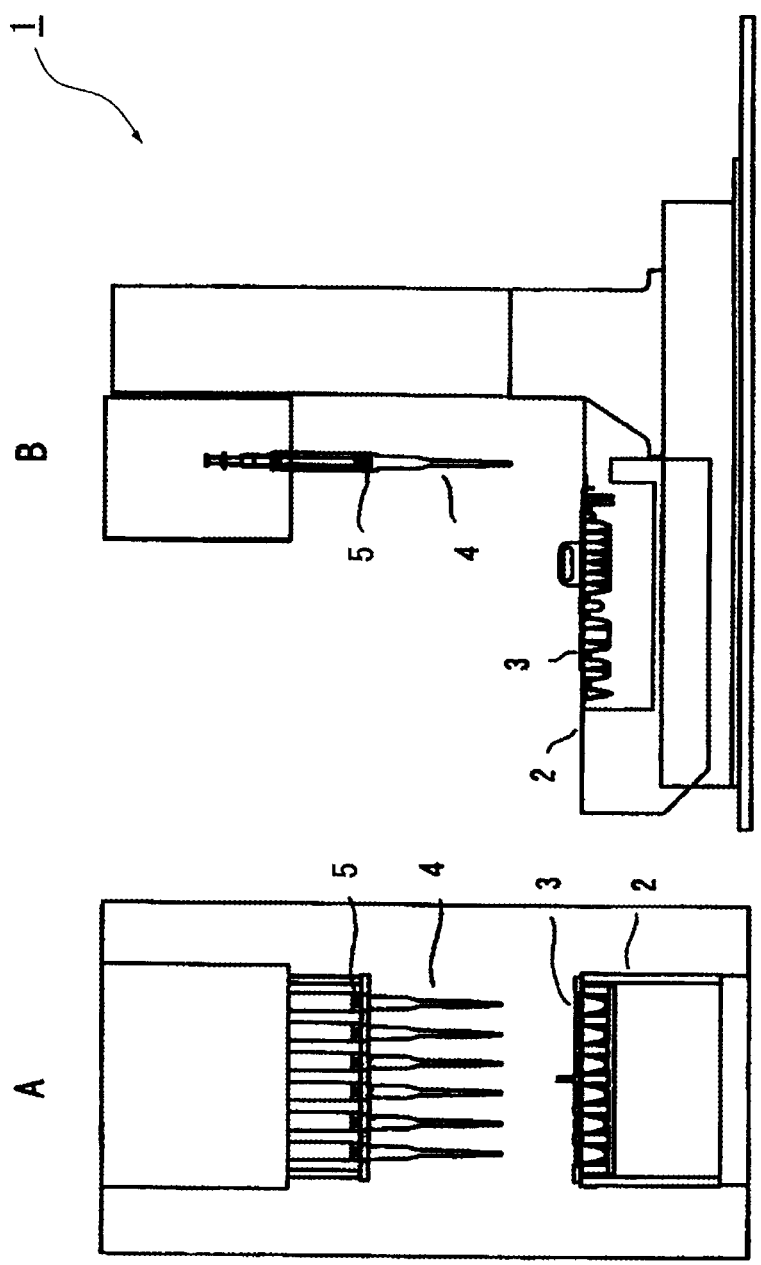
FIG. 1 is a front view (A) and a side view (B) which schematically illustrate an embodiment of an automatic analyzer to which the determining method of the present invention may be applied.

The automatic analyzer 1 shown in FIG. 1 comprises a measuring table 2 on which one or more cartridges 3 having plural wells for samples and/or reagents for detection can be placed. A line of plural nozzles 5, in which tips 4 can be mounted and liquid can be aspirated and poured out by means of the tips 4, are placed over the measuring table. The nozzles 5 can be moved up and down in the vertical direction. When the bottom end of the tip 4 is located at the lowest position, an aspiration of liquid from wells of the cartridge 3, pouring of liquid to wells thereof, mixing of liquid in the wells by continuously repeating aspiration and injection, or the like can be carried out. Further, wells of interest can be placed directly below the nozzles by moving the measuring table 2 in the horizontal direction. If desired, one or more magnets (not shown in FIG. 1) capable of being brought into contact with the outer sidewalls of tips 4 may be positioned. In this case, magnetic particles as a reagent for detection, such as magnetic particles coated with an antibody specific to a compound to be analyzed, may be used together with the magnets to carry out a B/F separation in the tips.

As the means for supplying a sample to a reaction system, an aspiration/injection means in which a tip portion is integrated with a nozzle portion, a transfer means capable of aspirating a sample from one end thereof and transferring the sample from the other end thereof, or the like may be used, instead of the nozzles in which tips can be mounted as shown in FIG. 1. As the transfer means, there may be mentioned, for example, a tube such as a flexible tube or a capillary tube, or a channel. Hereinafter, the present invention will further explained with reference to embodiments equipped with the dispensing means in which a tip can be mounted and liquid can be aspirated and poured out by means of the tip, but is by no means limited to these embodiments.

Figure 2:
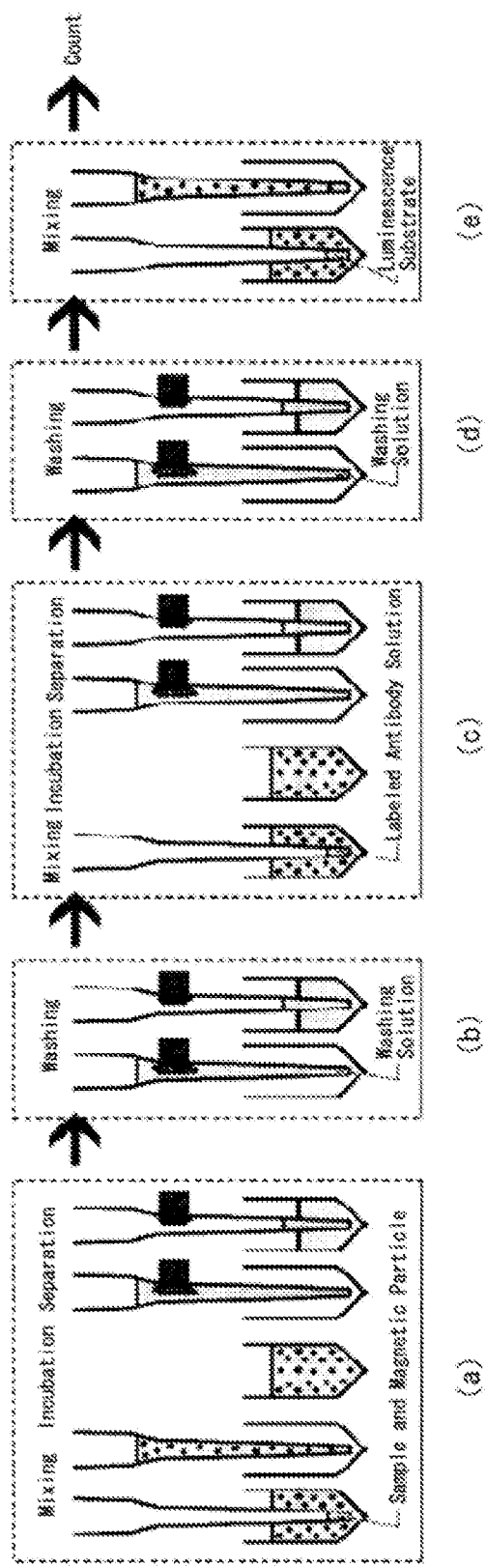
FIG. 2 schematically illustrates procedures of an embodiment of an automatic analyzing method to which the determining method of the present invention may be applied.

An embodiment of an automatic analyzing method using the automatic analyzer shown in FIG. 1 is shown in FIG. 2. In the automatic analyzing method shown in FIG. 2, magnetic particles coated with the first antibody, the second antibody labeled with an enzyme, and a luminescence substrate are used as reagent for detection, together with magnets capable of being brought into contact with the outer walls of tips, to carry out a B/F separation in the tips.

In the first step [(a) first reaction], a predetermined amount of a sample is added, by means of a tip, to the first well to which a predetermined amount of antibody-coated magnetic particles is previously dispensed, the sample and the antibody-coated magnetic particles are properly mixed by pipetting, and the mixture is incubated. After the antigen-antibody reaction has proceeded sufficiently, the reaction liquid is aspirated into the tip, and the reaction liquid is poured out while capturing the magnetic particles on the inner wall of the tip with a magnet.

In the second step [(b) washing], the tip is inserted in the second well to which a predetermined amount of a washing solution is previously dispensed, and the magnetic particles captured with the magnet are washed by pipetting of the washing solution.

In the third step [(c) second reaction], the tip is inserted in the third well to which a predetermined amount of an enzyme-labeled antibody solution is previously dispensed, the magnetic particles and the solution are properly mixed by pipetting of the labeled antibody solution, and the mixture is incubated. After the antigen-antibody reaction has proceeded sufficiently, the reaction liquid is aspirated into the tip, and the reaction liquid is poured out while capturing the magnetic particles on the inner wall of the tip with the magnet.

In the fourth step [(d) washing], the tip is inserted in the fourth well to which a predetermined amount of a washing solution is previously dispensed, and the magnetic particles captured with the magnet are washed by pipetting of the washing solution.

In the fifth step [(e) luminescence reaction], the tip is inserted in the fifth well to which a predetermined amount of a luminescence substrate solution is previously dispensed, and a luminescence reaction is carried out by pipetting of the substrate solution. After the reaction is carried out for a predetermined time, an amount of luminescence may be measured to determine an amount or concentration of a substance to be analyzed.

As a sample to be analyzed used in the present invention, there may be mentioned, for example, body fluids, particularly blood, such as whole blood, a serum, or plasma.

A substance to be analyzed contained in the sample is not particularly limited, so long as a substance which specifically binds with the analyte to form a reaction product can be selected. As a combination of the analyte and a substance specific thereto, there may be mentioned, for example, an antigen and an antibody, an antibody and an antigen, a protein and a ligand, or a sugar chain and a lectin, preferably an antigen and antibody, or an antibody and an antigen. The term "to specifically bind" used herein means to form a reaction product by biochemically and specifically binding with a subject. As the substance to be analyzed, there may be mentioned, for example, hepatitis B virus surface antigen (HBsAg), hepatitis C virus (HCV) antibody and antigen, human immunodeficiency virus (HIV) antibody, human T-cell leukemia virus-1 (HTLV-1) antibody, or *Treponema pallidum* (TP) antibody. Further, myocardial markers [for example, creatine kinase MB (CKMB), myoglobin, or troponin], hormones, serum proteins, or the like may be used.

A reaction system for measuring a sample is not particularly limited. For example, an immunoassay based on an antigen-antibody reaction may be preferably used.

The determination in the present invention is based on an optical technique. In the present invention, a sample is aspirated into a tip, and a portion in which the sample is held is irradiated with light. The optical intensity may be analyzed to determine whether or not the tip is mounted, whether or not the sample exists in the tip, and/or the kind of the sample.

More particularly, with respect to the tip for aspirating a sample, a portion in which the sample is held is irradiated with light, preferably before the aspiration and after the aspiration, and an optical change in, for example, transmission, reflection, or scattering may be detected with a well-known device such as a photodetector to determine whether or not the tip is mounted, whether or not the sample exists in the tip, and/or the kind of the sample.

When a tube or a channel comprising a transparent region composed of a transparent material is used as the supplying means, the transparent region is irradiated with light, and an optical intensity, which varies according to the presence or absence of the sample and/or the kind of the sample transferred in the tube or the channel, may be analyzed to determine the presence or absence of the sample and/or the kind of the sample.

As shown in the experimental data of Examples 1 and 2 described below, an amount of transmitted light when a tip is not mounted (hereinafter referred to as the unmounted-tip case) is larger than that when a tip is mounted and no sample is aspirated into the tip (hereinafter referred to as the mounted-tip case), and thus, it is possible to determine whether or not a tip is mounted by measuring an amount of transmitted light.

Further, since little light is transmitted when whole blood is aspirated into a tip (hereinafter referred to as whole-blood-holding case), an amount of transmitted light in the whole-blood-holding case becomes smaller than that in the mounted-tip case. In contrast, an amount of transmitted light when plasma or a serum is aspirated into a tip (hereinafter referred to as plasma-or-serum-holding case) becomes larger than that in the mounted-tip case, due to the lens effect caused by a tip, but does not exceed that in the unmounted-tip case.

These cases can be arranged in order of the decreasing amount of transmitted light as follows:

unmounted-tip case>plasma-or-serum-holding case>mounted-tip case>whole-blood-holding case.

Therefore, it is possible to determine whether or not a tip is mounted, whether or not a sample exists in a tip, and/or the kind of a sample, by using an amount of transmitted light as an index. In the unmounted-tip case, an inadequate operation, such as a failure in preparing tips, a failure in mounting a tip, or the like, can be detected. In the mounted-tip case, an inadequate operation, such as a failure in preparing samples, a failure in setting one or more samples, or the like, can be detected. Each threshold may vary according to conditions, such as the kind of an optical analyzing system, properties (for example, materials, the quality of materials, shape, or size) of a tip, or the like, and thus, is not particularly limited. Those skilled in the art can easily determine each threshold without undue experimentation by carrying out a pilot test, for example, by measuring amounts of transmitted light in these cases in accordance with the procedures described in Examples 1 to 2.

With respect to three cases that a sample is (1) whole blood, (2) plasma or a serum, and (3) an inadequate operation (for example, a failure in setting one or more samples), an embodiment of a logic for determination will be explained below.

First, a pilot test using plural whole blood and plasma and/or sera is carried out to measure amounts of transmitted light when a sample is aspirated into a tip (i.e., an amount of transmitted light in the whole-blood-holding case, and an amount of transmitted light in the plasma-or-serum-holding case). Further, an amount of transmitted light (To) in the mounted-tip case (i.e., when no sample is aspirated into a tip) is measured. As described above, the order of the decreasing amount of transmitted light is as follows:

plasma-or-serum-holding case>mounted-tip case>whole-blood-holding case.

On the basis of these measurement values, a threshold between the plasma-or-serum-holding case and the mounted-tip case (hereinafter referred to as threshold a) and a threshold between the mounted-tip case and the whole-blood-holding case (hereinafter referred to as threshold b) are determined in advance.

Next, to determine a unknown sample, the tip is irradiated with light to measure an amount of transmitted light (T). When the amount of transmitted light T of the unknown sample is larger than the threshold a, it is possible to determine that this is the plasma-or-serum-holding case, i.e., that the unknown sample is plasma or a serum. When the amount of transmitted light T of the unknown sample is smaller than the threshold b, it is possible to determine that this is the whole-blood-holding case, i.e., that the unknown sample is whole blood. When the amount of transmitted light T of the unknown sample is between the threshold a and the threshold b, it is possible to determine that there is an inadequate operation.

The above logic for determination (hereinafter sometimes referred to as the one-step method) which may be used in the present invention comprises, for example, the steps of:

(A) comparing an optical intensity (for example, an amount of transmitted light) measured in a supplying step (for example, when a sample to be determined is aspirated into a supplying means such as a tip) with the previously determined threshold a (i.e., the threshold between an optical intensity when plasma or a serum is aspirated into the supplying means and an optical intensity when no sample is aspirated into the supplying means) and the previously determined threshold b (i.e., the threshold between an optical intensity when no sample is aspirated into the supplying means and an optical intensity when whole blood is aspirated into the supplying means); and (B) determining that when the optical intensity of the sample is higher than the threshold a, the sample is plasma or a serum; when the optical intensity thereof is lower than the threshold b, the sample is whole blood; and when the optical intensity thereof is between the threshold a and the threshold b, no sample is aspirated into the supplying means (for example, an inadequate operation).

According to the present invention, even if a sample is a hemolytic sample or a usual chyle sample (i.e., a whitish and opaque sample having a high lipid content), plasma or a serum can be clearly discriminated from whole blood, as shown in the experimental data described in Example 2. In this connection, when a chyle plasma or serum sample having an extremely high lipid content is used, it is sometimes difficult to discriminate the sample from whole blood. For example, when a chyle sample having an extremely high lipid content is used, an amount of transmitted light is sometimes a value between the threshold a and the threshold b (i.e., judged as an inadequate operation) or smaller than the threshold b (i.e., judged as whole blood) in the above-mentioned logic for determination. In such a case, when samples to be analyzed include (or are suspected of including) one or more chyle samples having an extremely high lipid content, a chyle plasma or serum sample can be discriminated from whole blood by diluting the sample(s) to, for example, 1.2-fold to 10-fold, preferably 1.5-fold to 5-fold, more particularly 2-fold, and measuring again an amount of transmitted light of the diluted sample(s). That is, when the sample is whole blood, there is little change between the values measured before the dilution and after the dilution, and when the sample is chyle plasma or serum, the value measured after the dilution is increased, and thus, a chyle plasma or serum sample can be discriminated from whole blood.

More particularly, when the amount of transmitted light T of an unknown sample (in undiluted form) is smaller than the threshold b (a usual sample is judged as whole blood) in the above-mentioned logic for determination, the unknown sample is diluted, and an amount of transmitted light of the diluted sample (hereinafter referred to as the amount of transmitted light T') is measured again under the same conditions. In this case, when the unknown sample is a chyle plasma or serum sample, the amount of transmitted light measured after the dilution is increased. In contrast, when the unknown sample is whole blood, there is little change between the values measured before the dilution and after the dilution. Therefore, such an unknown sample can be discriminated by previously determining a threshold c, with respect to the difference (T'−T) between the amount of transmitted light after the dilution (T') and that before the dilution (T). That is, when the difference "T'−T" is larger than the threshold c, the unknown sample may be judged as a chyle plasma or serum sample, and when the difference "T'−T" is not more than the threshold c, the unknown sample may be judged as whole blood.

Similarly, when the amount of transmitted light T of an unknown sample (in undiluted form) is between the threshold a and the threshold b (a usual sample is judged as that when no sample is aspirated into a tip) in the above-mentioned logic for determination, the unknown sample is diluted, and the amount of transmitted light T' is measured again under the same conditions. When the unknown sample is a chyle plasma or serum sample, the amount of transmitted light measured after the dilution is increased. In contrast, when no sample is aspirated into a tip, there is little change between the values measured before the dilution and after the dilution. Therefore, such an unknown sample can be discriminated by previously determining a threshold d, with respect to the difference (T'−T) between the amount of transmitted light after the dilution (T') and that before the dilution (T). That is, when the difference "T'−T" is larger than the threshold d, the unknown sample may be judged as a chyle plasma or serum sample, and when the difference "T'−T" is not more than the threshold d, it may be judged that no sample is aspirated into a tip.

As above, another logic for determination (hereinafter sometimes referred to as the two-step method) which may be used in the present invention comprises, for example, the steps of:

(A) comparing an optical intensity (for example, an amount of transmitted light) T measured in a supplying step (for example, when a sample to be determined is aspirated into a supplying means such as a tip) with the previously determined threshold a (i.e., the threshold between an optical intensity when plasma or a serum is aspirated into the supplying means and an optical intensity when no sample is aspirated into the supplying means) and the previously determined threshold b (i.e., the threshold between an optical intensity when no sample is aspirated into the supplying means and an optical intensity when whole blood is aspirated into the supplying means);

(B') determining that, when the optical intensity of the sample is higher than the threshold a, the sample is judged as plasma or a serum; when the optical intensity thereof is lower than the threshold b, the following step (C) is carried out; and when the optical intensity thereof is between the threshold a and the threshold b, the following step (D) is carried out;

(C) diluting the sample, and comparing the difference (T'−T) between the optical intensity T' measured under the same conditions and the optical intensity T, with the previously determined threshold c (i.e., a threshold between the difference "T'−T" when a sample is a chyle plasma or serum sample and the difference "T'−T" when a sample is whole blood), to determine that, when the "T'−T" is larger than the threshold c, the sample is judged as a chyle plasma or serum sample, and when the difference "T'−T" is not more than the threshold c, the unknown sample is judged as whole blood; and (D) diluting the sample, and comparing the difference (T'−T) between the optical intensity T' measured under the same conditions and the optical intensity T, with the previously determined threshold d (i.e., a threshold between the difference "T'−T" when a sample is a chyle plasma or serum sample and the difference "T'−T" when no sample is aspirated into the supplying means), to determine that, when the "T'−T" is larger than the threshold d, the sample is judged as a chyle plasma or serum sample, and when the difference "T'−T" is not more than the threshold d, it is judged that no sample is aspirated into the supplying means (for example, an inadequate operation).

The logic for determination in the two-step method is shown in Table 1.

TABLE 1

| Step B' | T < b<br>to StepC | | b ≤ T ≤ a<br>to Step D | a < T<br>P/S |
|---|---|---|---|---|
| Step C | ΔT ≤ c<br>WB | c < ΔT<br>P/S | | |
| Step D | | | ΔT ≤ d<br>IO | d < ΔT<br>P/S |

WB: whole blood
P/S: plasma or a serum
IO: inadequate operation

In the present invention, the one-step method or the two-step method may be appropriately selected and carried out according to the state of samples (a set of samples) to be analyzed. For example, when the samples to be analyzed include no chyle sample having an extremely high lipid content, the one-step method is preferable. A chyle sample can be identified by, for example, a visual check. According to the one-step method, a convenient and rapid analysis can be carried out, because the judgment is made in one step. When the samples to be analyzed include (or are suspected of including) one or more chyle samples having an extremely high lipid content, the two-step method is preferable. According to the two-step method, a more accurate analysis can be carried out, and a visual check of samples is not necessary. The effect of chyle (lipid content in samples) was examined using intrafat (20%, Takeda Chemical Industries, Ltd.) and, as a result, the type of samples having a lipid content of 300 mg/dL or less could be determined by the one-step method of the present invention. Further, with respect to samples having a lipid content of more than 300 mg/dL, it was confirmed that the type of samples having a lipid content of 1500 mg/dL or less could be determined (particularly, discriminated from whole blood) by the two-step method (2-fold dilution).

Figure 3:
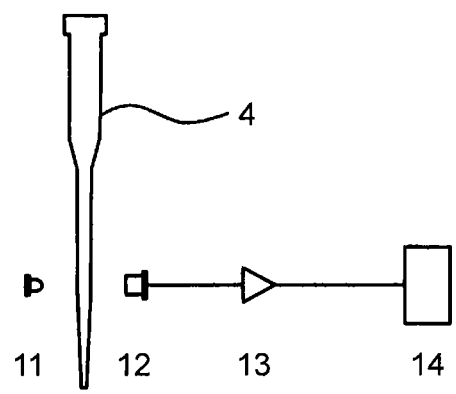
FIG. 3 schematically illustrates an embodiment of an optical analyzing system which may be used in the present invention.
Figure 4:
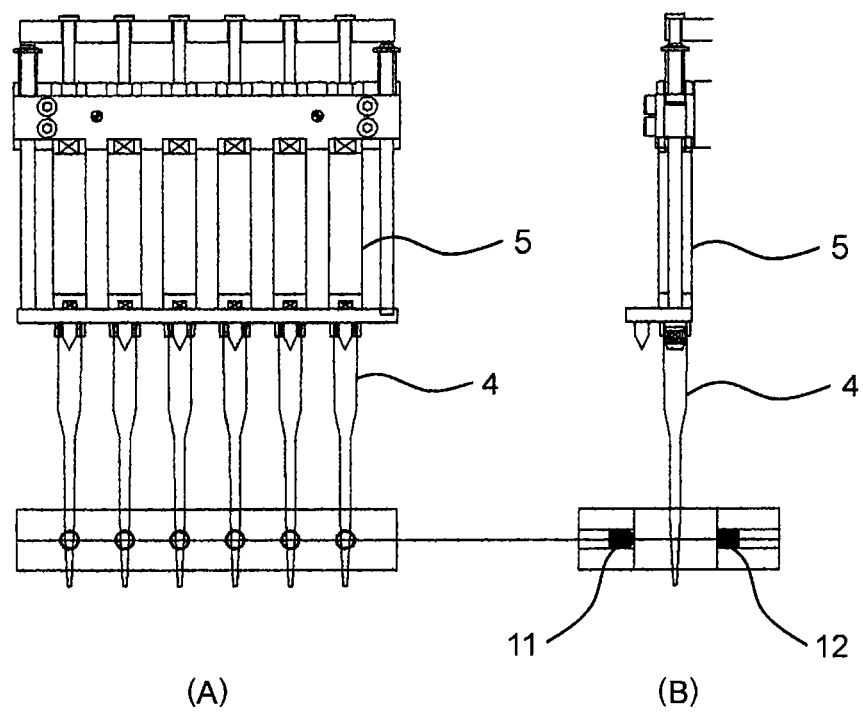
FIG. 4 is an enlarged partial front view (A) and an enlarged partial side view (B) which schematically illustrate a state in which an embodiment of an optical analyzing system which may be used in the present invention is incorporated into an automatic analyzer.

An embodiment of an optical analyzing system (transmission type) which may be used in the present invention is shown in FIGS. 3 and 4.

As shown in FIG. 3, a light emitting diode (LED) 11 and a photodiode (PD) 12 are located opposite to each other and spaced apart, so that a tip 4 can be placed therebetween. As the tip, a material through which light can be transmitted may be used, and there may be mentioned, for example, glass or transparent plastics, such as polyethylene, polystyrene, polycarbonate, polyacrylic plastics, or polypropylene. The inner diameter, wall thickness, material, or the like of the tip, and the light intensity, optical path length, or the like of the light may be appropriately selected to optimize the optical system. For example, when polypropylene tips are used, the portion to be irradiated with light has an outer diameter of preferably 2 to 10 mm, more preferably 3 to 6 mm, an inner diameter of preferably 1 to 8 mm, more preferably 2 to 4 mm, and a wall thickness of preferably 0.2 to 2 mm, more preferably 0.5 to 1 mm. In this connection, the present invention is not limited to these values.

The wavelength of the photodiode is not limited, so long as at least the unmounted-tip case, the plasma-or-serum-holding case, the mounted-tip case, and the whole-blood-holding case are optically discriminated from each other. The wavelength of light emitted from a commonly used photodiode includes an ultraviolet region, a visible region, and an infrared region, and an appropriate wavelength may be selected therefrom. For example, a visible region of 380 to 780 nm may be preferably used, more preferably 400 to 700 nm, most preferably 470 to 635 nm. In this connection, the present invention is not limited to these wavelength ranges.

With respect to the irradiation angle of light, it is preferable to irradiate the tip with light at a right angle to the tip. When the irradiation angle is not a right angle, the present invention can be carried out by using a means for compensating a refractive index caused when the light is transmitted through the tip and the sample.

As a means for detecting the transmitted light, a well-known detecting means may be used, with appropriate modifications if desired. For example, the light output from the light source (LED) 11 is transmitted through the tip, the amounts of light (current value) detected with the photodetector (photodiode) 12 are current-voltage converted by the operational amplifier 13, the analog values are digitalized with the AD converter 14, and the digital values are processed with software.

In this procedure, digital values or levels according to the types of samples and the presence or absence of the tip can be input as the thresholds in advance.

In the present invention, as an optical analyzing system other than that shown in FIGS. 3 and 4, for example, an image processing system using a CCD camera may be used.

In the image processing system using a CCD camera, the detected light can be captured as color information by passing the light through an RGB primary-colors filter, and the sample can be determined by color. When the RGB primary-colors filter is not used, it can be determined from gradations in monochrome whether or not the light is transmitted.

EXAMPLES

The present invention now will be further illustrated by, but is by no means limited to, the following Examples.

Example 1

Determination of Whole Blood and Plasma by Various Wavelengths

In this example, the system shown in FIGS. 3 and 4 for analyzing transmitted light was used to determine whole blood and plasma.

As a light emitting diode (LED), three types of LEDs, i.e., an LED having a peak wavelength of 635 nm (GL3HD44; Stanley), an LED having a peak wavelength of 573 nm (NSPY800AS; NICHIA), and an LED having a peak wavelength of 470 nm (NSPB500S; NICHIA), were used. As a photodiode (PD), a PD having a sensitivity wavelength range of 320 to 1100 nm (S6775; Hamamatsu Photonics) was used.

As a tip, polypropylene tips having a portion (outer diameter=3.6 mm, inner diameter=2.2 mm, and wall thickness=0.7 mm) irradiated with light were used.

As a sample aspirated into the tip, water (purified water), plasma, and whole blood were used. With respect to the cases that the tip was not mounted, that the tip was mounted, and that one of the samples was aspirated into the tip, an amount of transmitted light was measured using the system shown in FIGS. 3 and 4. The results are shown in Table 2. The unit used in Table 2 is output voltage (V).

As shown in Table 2, a detected value of light was highest when the tip was not mounted (i.e., control), and the detected value of light was lowered by mounting the tip. Whereas the detected value of light was further lowered when whole blood was aspirated into the tip, the detected value of light was increased due to the lens effect caused by the tip when water or plasma was aspirated into the tip, in comparison with the case of the tip alone.

It was clarified from these results that whole blood can be discriminated from plasma by measuring the detected value of light. Further, the difference between the value obtained in the case of the tip alone and that of the tip and plasma was enough to discriminate one from the other, and thus, the cases of no tip, tip alone, plasma, and whole blood can be discriminated automatically. In this connection, similar results were obtained with respect to a serum.

TABLE 2

|  | 470 nm | 575 nm | 635 nm |
|---|---|---|---|
| Control | 3.52 | 3.49 | 3.29 |
| Tip alone | 0.94 | 1.17 | 1.26 |
| Tip and water | 1.73 | 2.13 | 2.12 |
| Tip and plasma | 1.39 | 1.99 | 2.04 |
| Tip and whole blood | 0.17 | 0.12 | 0.69 |

Example 2

Determination of Various Samples

In this example, the procedures described in Example 1 were repeated, except that an LED having a peak wavelength of 590 nm (EFY3863; Stanley) was used as an LED for a light source.

Plasma, plasma supplemented with commercially available interfering substances (purchased from Sysmex Corporation), whole blood, and water were used as samples. The interfering substances used and final concentrations (or turbidity) thereof are as follows:

bilirubin (concentration=25 mg/dL, 50 mg/dL, and 75 mg/dL)

hemoglobin (concentration=500 mg/dL, 750 mg/dL, 1000 mg/dL, and 1500 mg/dL)

chyle (formazin turbidity) (concentration=1500 degree, 3000 degree, and 4500 degree)

With respect to the cases that the tip was not mounted, that the tip was mounted, and that one of the samples was aspirated into the tip, an amount of transmitted light was measured in accordance with the procedure described in Example 1. Each sample was measured 18 times, and the averages thereof are shown in Table 3. The unit used in Table 3 is output voltage (V).

As shown in Table 3, a detected value of light was highest when the tip was not mounted, and the detected value of light was lowest when whole blood was aspirated in the tip. Detected values of light when liquid (plasma, plasma supplemented with bilirubin, plasma supplemented with hemoglobin, plasma supplemented with chyle, or water) was aspirated were between that in the control and that in the whole-blood-holding case. These results indicate that whole blood can be discriminated from plasma by measuring the detected value of light. Further, it was clarified from these results that, even if plasma is colored with hemolysis or the like, or plasma is an opaque plasma having a high lipid content, whole blood can be clearly discriminated from such plasma.

TABLE 3

| Samples to be measured | Output voltage |
| --- | --- |
| control (no tip) | 2.99 |
| tip alone | 0.88 |
| water | 2.10 |
| plasma | 1.88 |
| with bilirubin, 25 mg/dL | 1.92 |
| with bilirubin, 50 mg/dL | 1.94 |
| with bilirubin, 75 mg/dL | 1.93 |
| with hemoglobin, 500 mg/dL | 1.89 |
| with hemoglobin, 750 mg/dL | 1.92 |
| with hemoglobin, 1000 mg/dL | 1.83 |
| with hemoglobin, 1500 mg/dL | 1.82 |
| with chyle (turbidity), 1500 degree (FTU) | 1.84 |
| with chyle (turbidity), 3000 degree (FTU) | 1.87 |
| with chyle (turbidity), 4500 degree (FTU) | 1.74 |
| whole blood | 0.66 |

Example 3

Discrimination Between Chyle Sample and Whole Blood

The following procedure was carried out in accordance with the procedures described in Example 2.

Intrafat (20%, Takeda Chemical Industries, Ltd.) was used to prepare samples having concentrations (lipid) shown in Table 4. These samples and whole blood were used as samples.

With respect to the cases that one of samples (the above-mentioned samples and the double-diluted samples thereof) was aspirated into the tip, an amount of transmitted light was measured in accordance with the procedure described in Example 1. Each sample was measured 18 times, and the averages thereof are shown in Table 4. The unit used in Table 4 is output voltage (V).

As shown in Table 4, it was clarified that samples suspected of being misidentified as whole blood due to the effect of chyle (300 mg/dL or more) can be clearly discriminated from whole blood by the two-step method.

TABLE 4

| Samples | One-step method Output voltage | Two-step method Output voltage |
| --- | --- | --- |
| 200 mg/dL | 1.64 | 1.92 |
| 300 mg/dL | 1.23 | 1.89 |
| 350 mg/dL | 1.01 | 1.88 |
| 500 mg/dL | 0.79 | 1.80 |
| 1000 mg/dL | 0.73 | 1.74 |
| 1500 mg/dL | 0.70 | 1.71 |
| Whole blood | 0.67 | 0.65 |

INDUSTRIAL APPLICABILITY

The present invention may be applied to an automatic analysis of samples such as body fluids.

Although the present invention has been described with reference to specific embodiments, various changes and modifications obvious to those skilled in the art are possible without departing from the scope of the appended claims.

The invention claimed is:

1. A method for analyzing a substance, comprising a supplying step and an analyzing step,
   the supplying step comprising the steps of:
   supplying a sample suspected of containing the substance to be analyzed to a reaction system by a supplying means comprising a transparent region composed of a transparent material, wherein the sample is selected from the group consisting of whole blood, a serum, and plasma,
   irradiating the transparent region with light, and
   measuring an optical intensity T of a transmitted light from the transparent region,
   the analyzing step comprising the steps of:
   reacting a reagent for detecting the substance with the sample in the reaction system, and
   analyzing a signal derived from a product obtained by the reaction,
   wherein the supplying means is one in which a tip comprising the transparent region is mounted, or a tube or a channel comprising the transparent region, and the transparent region exhibits a lens effect that an optical intensity when plasma or a serum is aspirated into the transparent region is higher than an optical intensity when no sample is aspirated into the transparent region, and
   wherein after the measuring step in the supplying step, the supplying step further includes the steps of:
   (A) comparing the optical intensity T with previously determined threshold a between an optical intensity when plasma or a serum is aspirated into the supplying means and an optical intensity when no sample is aspirated into the supplying means, and with previously determined threshold b between an optical intensity when no sample is aspirated into the supplying means and an optical intensity when whole blood is aspirated into the supplying means,
   (B') determining that, when the optical intensity T of the sample is higher than the threshold a, the sample is judged as plasma or a serum; when the optical intensity thereof is lower than the threshold b, the following step (C) is carried out; and when the optical intensity thereof is between the threshold a and the threshold b, the following step (D) is carried out,
   (C) diluting the sample, and comparing the difference "T'– T" between an optical intensity T' measured under the same conditions and the optical intensity T, with previously determined threshold c between the difference "T'−T" when a sample is a chyle plasma or serum sample and the difference "T'−T" when a sample is whole blood, to determine that, when the "T'−T" is larger than the threshold c, the sample is judged as a chyle plasma or serum sample; and when the difference "T'−T" is not more than the threshold c, the sample is judged as whole blood, and (D) diluting the sample, and comparing the difference "T'−T" between the optical intensity T' measured under the same conditions and the optical intensity T, with previously determined threshold d between the difference "T'−T" when a sample is a chyle plasma or serum sample and the difference "T'−T" when no sample is aspirated into the supplying means, to determine that, when the "T'−T" is larger than the threshold d, the sample is judged as a chyle plasma or serum sample; and when the difference "T'−T" is not more than the threshold d, it is judged that no sample is aspirated into the supplying means.

2. The method according to claim 1, wherein the supplying means is a dispensing means in which a pipette tip can be mounted and liquid can be aspirated and poured out by means of the tip.

* * * * *